United States Patent [19]

Weinstein et al.

[11] 4,078,056
[45] Mar. 7, 1978

[54] ANTIBIOTIC COMPLEX FROM MICROMONOSPORA ARBORENSIS

[75] Inventors: Marvin J. Weinstein; Gerald H. Wagman, both of East Brunswick; Joseph A. Marquez, Montclair; Raymond T. Testa, Verona, all of N.J.

[73] Assignee: Schering Corporation, Kenilworth, N.J.

[21] Appl. No.: 654,327

[22] Filed: Feb. 2, 1976

Related U.S. Application Data

[63] Continuation-in-part of Ser. No. 516,242, Oct. 18, 1974, abandoned.

[51] Int. Cl.$^2$ ............................................. A61K 35/74
[52] U.S. Cl. .................................. 424/117; 424/115; 195/80 R
[58] Field of Search .............. 424/115, 117; 195/80 R

[56] References Cited
PUBLICATIONS

Miller, The Pfizer Handbook of Microbial Metabolites, McGraw-Hill Book Co., Inc., N.Y., N.Y., 1961, pp. 595–596.

*Primary Examiner*—Jerome D. Goldberg
*Attorney, Agent, or Firm*—Carver C. Joyner; Stephen B. Coan; Raymond A. McDonald

[57] ABSTRACT

*Micromonospora arborensis* produces a plurality of antibiotics named herein antibiotic 68-1147 complex, when cultivated under controlled aerobic conditions. Two of the antibiotics, antibiotic 68-1147 I and antibiotic 68-1147 II are described and shown to be effective antibacterial agents, especially against gram positive bacteria.

6 Claims, No Drawings

ANTIBIOTIC COMPLEX FROM MICROMONOSPORA ARBORENSIS

This application is a continuation-in-part application of our copending application, Ser. No. 516,242, filed Oct. 18, 1974 (now abandoned).

This invention relates to a new antibiotic complex elaborated by a novel species of the genus Micromonospora. Mor particularly, this invention relates to antibiotic 68-1147 complex and to the microorganism which produces the same, namely, *Micromonospora arborensis*.

THE MICROORGANISM

*Micromonospora arborensis* sometimes referred to as *M. arborensis* was isolated from a soil sample collected in Ann Arbor, Michigan and on the basis of its taxonomical and physiological properties has been determined to be a new species of Micromonospora.

A viable subculture of *Micromonospora arborensis* was deposited and can be obtained from the permanent collection of the Northern utilization and Research, Agricultural Research Service, U.S. Department of Agriculture, Peoria, Illinois where it was given the ascension No. NRRL 8041.

In addition to the description set forth in the tables below, a further distinguishing characteristic of *M. arborensis* is its ability to elaborate the antibiotic 68-1147 complex. This invention embraces *Micromonospora arborensis* NRRL 8041 and mutants and variants thereof having the distinguishing characteristics of *M. arborensis* NRRL 8041.

Thus, in one of its aspects this invention is directed to producing the antibiotic 68-1147 complex which comprises cultivating *Micromonospora arborensis* or a mutant or variant thereof having the identifying characteristics of NRRL 8041 in an aqueous nutrient medium under aerobic conditions until substantial antibiotic activity is imparted to said medium and isolating antibiotic 68-1147 complex therefrom.

In another of its aspects, this invention relates to the use of antibiotic 68-1147 complex or components thereof as antibacterial agents.

The taxonomical morphological and physiological characeristics set forth hereinbelow are derived from art recognized techniques utilizing standard media. In the description of the microorganism, two color designators are employed. The first is a color name taken from the "Descriptive Color Name Dictionary" by Taylor, Knoche and Granville published by the Container Corporation of America (1950) U.S.A., with a color chip number corresponding to the color name, the chip number being taken from "The Color Harmony Manual," 4th Edition, 1958, also published by the Container Corporation of America. The second designator consists of a color name and number which refers to the synonym and near synonym found in the National Bureau of Standards, Circular 553, November 1, 1965 (U.S.A.).

TABLE I

Medium: Yeast extract 0.1%, Dextrose 1.0%, CaCO$_3$ 0.1%, Agar 1.5%

| Organism | Observations Macroscopic | Microscopic |
|---|---|---|
| Micromonospora arborensis | Growth moderate, plicate, no aerial mycelium. g4Pc dusty orange, | Spores spherical to ovate, 0.8 microns average diameter. |

TABLE I-continued

Medium: Yeast extract 0.1%, Dextrose 1.0%, CaCO$_3$ 0.1%, Agar 1.5%

| Organism | Observations Macroscopic | Microscopic |
|---|---|---|
| | Moderate orange 53. | |

TABLE II

GROWTH CHARACTERISTICS

| | |
|---|---|
| Czapeks Medium (Glucose) | Growth fair to poor, flat, no aerial mycelium, no diffusible pigment. g3gc light tan, light yellowish brown 76. |
| Asparagine-Glucose Medium | Growth fair, granular, no aerial mycelium, faint yellow diffusible pigment produced. g4nc russet orange, strong orange 50. |
| Calcium Malate Agar | Growth fair to poor, flat, no aerial mycelium, no diffusible pigment. g3ic light amber, dark orange yellow 72. |
| Nitrate Reduction | Variable. |
| Ordinary Agar (water agar) | Growth poor, not recordable. |
| Nutrient Agar | Growth fair, to poor, flat, furrowed, no aerial mycelium, very faint yellow diffusible pigment produced. g3ic light amber, dark orange yellow 72. |
| Loffler's Serum Medium (Difco) | Growth fair, weakly plicate, no aerial mycelium, no diffusible pigment, substrate little decomposed. g41c dusty orange, moderate orange 53. |
| Potato Plug | Growth fair to poor. |
| Peptone Glucose Agar | Growth poor, rarely one or two isolated colonies developing, colonies, when present, plicate no aerial mycelium, diffusible pigment not apparent. g4nc russet orange, strong orange 50. |
| Egg Agar (Dorset Egg Medium - Difco) | Growth poor, substrate not decomposed. |
| Gelatin Medium | Growth poor, flat, no aerial mycelium, gelatin hydrolysis weak. |
| Starch Agar | Growth fair, flat, furrowed, no aerial mycelium, no diffusible pigments, starch hydrolyzed. g4pe orange rust, deep orange 51. |
| Tyrosine Medium | Growth poor, granular, no aerial mycelium, dark amber (reddish brown) diffusible pigment produced. Reaction positive. |
| Litmus Milk (Difco) | Milk poorly peptonized. |
| Cellulose Medium | Cellulose not decomposed. |
| Milk Agar | Growth moderate, plicate, no aerial mycelium, yellow diffusible pigment produced, milk hydrolyzed. g4nc russet orange, strong orange 50. |
| Sucrose | Utilized |
| Starch | Hydrolysis positive. |
| Temperature | Grows at 26 and 37° C but not at 50° C or above. |
| Bennett's Agar | Growth fair, moderately plicate, no aerial mycelium, light yellowish diffusible pigment produced. g4pc russet orange, strong orange 50. |
| Emerson's Agar | Growth fair to poor, flat, no aerial mycelium, light yellowish diffusible pigment produced. g4nc russet orange, strong orange 50. |
| Tomato Paste Oatmeal Agar | Growth moderate, plicate to furrowed, no diffusible pigment apparent. Periphery: g4nc russet orange, strong orange 55. Center: g4ni brown spice, moderate brown 58. |
| Tyrosine Agar | Growth poor flat, no aerial mycelium, dark reddish brown diffusible pigment abundantly produced. Reaction positive. |
| Observations at 2, 7, and 14 days (After Gordon and Smith J. Bact. 69:147) | |
| Peptone Iron Agar Observations at 2, 7, and 14 days | Growth fair, plicate-membranous, no aerial mycelium, yellow diffusible pigment produced, no reaction. |

TABLE II-continued

GROWTH CHARACTERISTICS g3ic light amber, dark orange yellow 72.

TABLE III

CARBOHYDRATE UTILIZATION

|  | Growth |
|---|---|
| Negative Control | Poor |
| D-Arabinose | poor |
| L-Arabinose | moderate |
| Dulcitol | poor |
| D-Galactose | moderate |
| D-Glucose | moderate |
| Glycerol | poor |
| I-Inositol | poor |
| B-Lactose | fair to poor |
| D-Levulose | moderate |
| D-Mannitol | poor |
| Mannose | moderate |
| Melibiose | fair to poor |
| Melizitose | poor |
| Raffinose | poor |
| L-Rhamnose | poor |
| D-Ribose | poor |
| Salicin | poor |
| Sucrose | moderate |
| D-Xylose | moderate |
| Cellulose | fair to poor |
| Starch | moderate |
| Sorbitol | poor |
| Control 0.5% yeast extract | poor |

TABLE IV

UTILIZATION OF NITROGEN SOURCES

| Nitrogen Source + 1% glucose | |
|---|---|
| 0.5% Difco Yeast Extract | Growth good, plicate, no aerial mycelium, faint yellowish diffusible pigment. g5pa bright orange, vivid orange 48. |
| 1.0% NZ Amine Type A | Growth moderate, plicate to membraneous, no aerial mycelium, faint yellowish diffusible pigment. g5nc burnt orange, strong reddish orange 35. |
| 1% Asparagine | Growth poor, not recordable. |
| 1% Glutamic Acid | Growth poor not recordable. |
| 1% Sodium Nitrate | Growth poor, not recordable. |
| 1% Ammonium Nitrate | Growth poor, not recordable. |

Antibiotic 68-1147 is produced when the elaborating microorganism, *M. arborensis* is grown in an aqueous nutrient medium under submerged aerobic conditions. For small amounts of antibiotic, e.g. microgram to milligram quantities, surface culture in bottles or shake flasks may be employed. Typically, the nutrient medium is liquid, contains a carbon source such as an assimilable carbohydrate and an assimilable nitrogen source, such as a proteinaceous material. Preferred carbon sources include glucose, mannitol, levulose, sucrose, starch, ribose and the like. Preferred nitrogen sources include corn steep liquor, yeast extract soybean meal, meat peptones, casein hydrolysate, beef extract and the like. It is advantageous to use combinations of these carbon and nitrogen sources to provide good growth and antibiotic production.

Production of Antibiotic 68-1147 may be effected at most temperatures conducive to satisfactory growth of the microorganism; e.g. between 20° and 40° C, preferably 28°-35° C. Ordinarily, optimum production is obtained in 3-5 days in shake flasks and from about 2 to about 7 days in larger vessels. The pH of the medium is maintained between 6.0 and 8.5 during the fermentation, a pH of between 7 to 8 being preferred. Prior to sterilization and inoculation, the fermentation medium is usually adjusted to pH 7.0, re-adjustments being made as required during the course of the fermentation. Alternatively, the pH may be maintained at about 7.0 by the use of buffering agents such as calcium carbonate. These buffering agents generally tend to persist throughout the course of the fermentation.

When growth is carried out in large vessels and tanks, it is desirable to produce a vegetative inoculum of about 5% of the volume of the tank by inoculating the broth culture with a slant culture or a lyophilized culture of the organism. The inoculum stage of the fermentation usually requires from about 24 to about 120 hours with about 1 to 2 days being preferred. When a vigorously growing inoculum has been obtained, it is transferred aseptically to the larger vessel or tank containing sterile medium. During the course of the inoculum stage and the fermentation stage which follows, the tendency of the medium to foam is controlled by the addition of a suitable anti-foaming agent, such as, Dow Corning B ®, The Dow Chemical Company, Midland, Michigan.

The medium in which the vegetative inoculum is produced may be identical to that utilized for the production of antibiotic or it may differ so long as the medium is one in which good growth of the microorganism is obtained.

Variations in the ratio of components of the antibiotic 68-1147 complex are observed when changes are made in the fermentation conditions. In fact, one component which is normally produced in inconsequential amounts is abundantly produced when the medium designated C below is employed as the fermentation medium. Thus, it is advisable to monitor the course of the fermentation by chromatography and bioautography in addition to performing assays at intervals.

The following media are useful for the production of the Antibiotic 68-1147 complex. Media A, B and C are especially suitable for antibiotic production whereas medium D is particularly useful for the preparation of the vegetative inoculum.

| A | Yeast extract (General Biochemicals) | 10 gm |
|---|---|---|
|   | Mor-rex (Corn Products) | 30 gm |
|   | Calcium carbonate | 4 gm |
|   | Cobalt chloride | 130 μg |
|   | Tap water | 1000 ml |
| B | South African Fish solubles | 10 gm |
|   | Mor-rex | 30 gm |
|   | Calcium carbonate | 4 gm |
|   | Cobalt chloride | 130 μg |
|   | Tap water | 1000 ml |
| C | Yeast extract (Difco) | 5 gm |
|   | N-Z amine (Sheffield Chemical) | 5 gm |
|   | Mor-rex | 30 gm |
|   | Calcium carbonate | 4 gm |
|   | Cobalt chloride | 130 μg |
|   | Tap water | 1000 ml |
| D | Beef extract | 3 gm |
|   | Tryptose | 5 gm |
|   | Yeast extract | 5 gm |
|   | Dextrose | 1 gm |
|   | Starch | 24 gm |
|   | Calcium carbonate | 2 gm |
|   | Tap water | 1000 ml |

The foregoing media are exemplary of the nutrients utilized by *M. arborensis* to produce antibiotic 68-1147 complex. However, it is obvious to those skilled in the fermentation art that a wide range of nutrients obtained from a number of suppliers may be substituted for the foregoing, and that generally good growth and antibiotic production can be obtained, such nutrients being the functional equivalent of those set forth herein.

Peak antibiotic production is determined on the basis of a cylinder cup assay using *Staphyloccus aureus* ATCC 6538P as the test organism. The physical conditions for the assay and the assay itself are substantially similar to that used for determining the antibiotic potency of samples containing penicillin. A suitable reference standard is one wherein 1 μg of material gives a zone of inhibition of 14.9 ±1.2 mm and may be assigned a potency of 1000 μg/mg.

When peak production is attained, the antibiotic complex may be isolated by methods known in the art. Extraction with a non-water miscible polar organic solvent is a preferred method for isolating the antibiotic complex. Extraction of the antibiotic complex is usually followed by concentration of the extracts and precipitation of the antibiotic by the addition of a non-polar organic solvent such as low molecular weight hydrocarbons.

Comparison of the antibiotic complex with other known antibiotics having substantial activity against Gram positive organisms via paper and/or thin layer chromatography and subsequent bioautography indicates the complex to be novel. The compounds with which the comparison was conducted included macrolides, penicillins, cephaosporins, actinomycins etc.

Antibiotic 68-1147 Complex

The antibiotic complex consists of a plurality of active components, however, only two have been produced in sufficient quantity for isolation and characterization. These two have been designated antibiotic 68-1147 I and antibiotic 68-1147 II the latter being a chromatographically slower moving and presumably a more polar component. In most, although not all, fermentations the component i.e. 68-1147 I is produced in greater abundance. Both component appear to contain the following amino acids: threonine, proline, alanine, cysteine, isoleucine and tyrosine.

TABLE V

| Physicochemical Properties of Antibiotics 68-1147 I and II | |
|---|---|
| 68-1147 I | 68-1147 II |
| M.P. 229°–231° C dec. | M.P. ≅ 300° C dec. |
| λ max 202 mμ   53.55 | λ max 240 mμ |
| 247 mμ $\Sigma^{1\%}_{cm}$ 32.55 | 300 mμ $\Sigma^{1\%}_{cm}$ 18.84 |
| 308 mμ   10.72 |   5.42 |
| $[\alpha]_D^{26°} = -87.5°$ | $[\alpha]_D^{26°} = -65.5°$ |
| (C, 0.4%, dioxane) | (C, 0.4%, dioxane) |
| Elemental analysis | Elemental analysis |
| C, 49.46, H, 5.20; N, 14.88; O, 16.18; S, 10.47 | C, 50.24; H, 4.98; N, 15.87; O, 16.24; S, 12.67 by difference |
| The antibiotic has: an Infrared spectrum in mineral oil (Nujol) having characteristic absorption at: | |
| 3.05 m,sp | 9.00 w,sp |
| 3.45 s,sp | 9.15 w,br |
| 5.78 w,sp | 9.50 w,br |
| 6.08 s | 9.40 w,br |
| 6.31 w,sp | 9.75 w,sp |
| 6.60 s | 9.95 sh |
| 6.65 s | 10.58 w,br |
| 6.75 s | 10.70 w,br |
| 7.30 m,sp | 11.20 w,br |
| 7.45 sh | 11.30 sh |
| 7.65 w,sp | 11.90 microns w,br |
| 8.30 w,sp | | s = strong, m = medium, w = weak, sp = sharp, br = broad, sh = shoulder

Biological Properties of Antibiotic 68-1147 I and II

In Tables VI and VII are set forth the in vitro antibacterial spectrum of antibiotic 68-1147 I against a variety of microorganisms, including numerous resistant strains and against representative "anaerobes". The tests were performed via conventional tube dilution methods in Mueller-Hinton Broth.

Table VIII sets forth in vivo activity of antibiotic 68-1147 I in mice via subcutaneous and/or oral administration.

Table IX sets forth the in vitro antibacterial spectrum of antibiotic 68-1147 II against a variety of microorganisms.

TABLE VI

In Vitro Antibacterial Activity of Antibiotics 68-1147 I in Mueller-Hinton Broth

| Organism | | MIC (mcg/ml) | Resistant To* |
|---|---|---|---|
| Staphylococcus aureus | 209P | 0.03 | — |
| | Gray | 0.03 | — |
| | 12 | 0.03 | — |
| | Wood | 0.03 | P, L, T, S |
| | Zeigler | 0.03 | P, L, T, S |
| | 512 | 0.08 | P, L, T, S |
| | 433 | 0.03 | P |
| | St. M. | 0.003 | P, L, Ceph, S |
| | 405 | 0.08 | P, L, Ceph, S, T |
| | 237 | 0.3 | P, L, Ceph, S, T |
| | 1613 | 0.08 | P, L, Ceph, S, T |
| | 428 | 0.08 | P, L, Ceph, S, T |
| | 1650N | 0.03 | P, L, Ceph, S, T |
| | 618 | 0.03 | P, L, Ceph, S, T, E, Ol |
| | 484 | 0.08 | P, L, Ceph, S, T, E, Ol |
| | 616 | 0.03 | P, L, Ceph, S, T, E, Ol |
| | 336 | 0.03 | P, L, Ceph, S, T, E, Ol |
| | 494 | 0.03 | P, L, Ceph, S, T, E, Ol |
| | 1141 | 0.03 | P, L, Ceph, S, T, E, Ol |
| | 1026 | 0.03 | P, L, Ceph, S, T, E, Ol |
| | 1179 | 0.03 | P, L, Ceph, S, T, E, Ol |
| | 468 | 0.03 | P, L, Ceph, S, T, E, Ol |
| | 979 | 0.03 | P, L, Ceph, S, T, E, Ol |
| | 282 | 0.03 | P, L, Ceph, S, T, E, Ol |
| | 618 | 0.03 | P, L, Ceph, S, T, E, Ol |
| Enterococcus | 685 | 0.03 | P, Ceph, L, T, S |
| | 999 | 0.03 | P, Ceph, L, T, S |
| Streptococcus pyogenes | C | 0.03 | |
| | 27 | 0.03 | |
| | 30 | 0.03 | |
| | 16295 | 0.03 | |
| | 6589 | 0.03 | |
| | 3045 | 0.03 | |
| | 5 | 0.03 | |
| | 3 | 0.03 | |
| | 6 | 0.03 | |
| Bacillus subtilis 6633 | | 0.03 | |
| E. Coli Sc | | >25 | |
| Klebsiella DA20 | | >25 | |
| Proteus sp 12453 | | >25 | |
| Pseudomonas aeruginosa Sc 8709 | | >25 | |
| Salmonella schottmuelleri | | >25 | |

*P = penicillin, L = lincomycin, T = tetracycline, S = sulfonamide, Ceph = cephalothin, E = erythromycin, Ol = oleandomycin

TABLE VII

In Vitro Activity of Antibiotic 68-1147 I Against Anaerobes

| Organism | MIC (mcg/ml) |
|---|---|
| Corynebacterium acnes | |
| 6923 | 0.8 |
| 6922 | 3.0 |
| 6912 | 0.8 |
| 6921 | 0.3 |
| 11827 | 0.3 |
| Bacteroides fragilis | 0.8 |
| Bacteroides melaninogenicus | 37.5 |
| Bacteroides corrodens | 3.0 |
| Clostridium septicium | 0.03 |
| Clostridium novyi | 0.03 |
| Peptostreptococcus sp. | 0.01 |

TABLE VIII

In Vivo Activity of Antibiotic 68-1147 I

| Infecting Organism | Route | PD$_{50}$ (mg/kg) |
|---|---|---|
| Staphylococcus aureus | | |
| Gray | S. C. | 0.2 |

TABLE VIII-continued

| In Vivo Activity of Antibiotic 68-1147 I | | |
|---|---|---|
| Infecting Organism | Route | PD$_{50}$ (mg/kg) |
| | Oral | >50 |
| Acute Toxicity | | |
| | Route | LD$_{50}$ (mg/kg) |
| | S. C. | >800 |

TABLE IX

| In Vitro Antibacterial Activity of Antibiotic 68-1147 II in Mueller-Hinton Broth | | |
|---|---|---|
| Organism | | MIC (mcg/ml) |
| Staphylococcus aureus | 209P | .005 |
| | Wood | .005 |
| | Ziegler | .005 |
| | 59N | .005 |
| Streptococcus pyogenes | C | .005 |
| | 27 | .005 |
| Bacillus subtilis 6623 | | .005 |
| Pseudomonas aeruginosa | NRRL 3223 | >25 |

Antibiotic 68-1147 complex and the components thereof are active against bacteria especially against gram-positive bacteria. The compounds are also active against certain species of anerobic bacteria. Thus, they may be used in combination with soaps and detergents to destroy or inhibit bacteria in hospitals especially in hospital lavatories and operating rooms. Additionally the antibiotics may be incorporated into formulations used for cleaning surgical instruments and the like. The antibiotic complex may also be used to treat infected laboratory animals to prevent the spread of infection.

EXAMPLE I

Production of Antibiotic 68–1147 Complex

A. Inoculum Preparation

Prepare a series of 300 ml shake flasks containing 70 ml of the following medium:

| Beef Extract | 3 g. |
|---|---|
| Tryptose | 5 g. |
| Yeast Extract | 5 g. |
| Dextrose | 1 g. |
| Starch | 24 g. |
| Calcium Carbonate | 2 g. |
| Tap water | 1000 ml. |

Adjust to pH 7.5 then sterilize the medium at 121° C (15 psig) for 20 minutes, cool to room temperature (20°–25° C. Add a loopful of *Micromonospora arboresnis* from an agar slant or 0.5 ml of whole broth from a previously prepared inoculum. Incubate with continual agitation at 250–300 rpm for 2 days at 28° C.

B. Fermentation

Prepare, sterilize, cool and adjust to pH 7.0 10 liters of the following medium in a 14 liter fermentor.

| Yeast Extract | 100 g. |
|---|---|
| Mor-rex (Corn Products) | 300 g. |
| Calcium Carbonate | 40 g. |
| Cobalt chloride | 1.3 g. |
| Tap water | 10 liters |

Inoculate the medium with 500 ml of inoculum, prepared as described in step A. Incubate the fermentation mixture at 28° C for from about 66 to about 90 hours, until peak antibiotic production is attained as determined by standard cylinder cup assay against *Staphylococcus aureus* ATCC 6538P.

C. Isolation

Extract the fermentation medium twice with an equal volume of ethyl acetate, concentrate the extract to a residue in vacuo dissolve the residue in acetone and pour the acetone solution into an ethyl ether:hexane mixture (3:2) with stirring to obtain thereby a buff colored precipitate assaying about 590 μg/mg.

Alternatively, the antibiotic complex may be isolated by counter current extraction of the fermentation broth followed by concentration and precipitation as just described.

EXAMPLE 2

Separation of Antibiotic 68-1147 Components

Dissolve 1 g of antibiotic 68-1147 complex, (prepared as described in Example 1) in a mixture of acetone:benzene (3:2) and "streak out" the solution on about 25 silica gel G.F. plates 500 microns in thickness. Subject the plates to chromatography using the above-described solvent mixture. Detect the location of the components on duplicate plates by bioautography, by exposure of the plates to iodine vapors determining thereby the existence of four active components having the following Rf values:

| 68-1147 I | (0.51) |
|---|---|
| 68-1147 II | (0.42) |
| 68-1147 III | (0.31) |
| 68-1147 IV | (0.03) |

Isolate the respective components by scraping the appropriate band from the silica gel plate. Component I (68-1147 I) the major component weighs 320 mg and is purified by rechromatography as described above to yield 162 mg assaying 2400 μg/mg.

EXAMPLE 3

Alternate Separation of Antibiotic 68-1147 Components

Precipitate a concentrate of an ethyl acetate extract obtained from a 50 gal. fermentation in to hexane to obtain a gummy precipitate. Dissolve the gum in chloroform and wash the solution with potassium hydrogen phthalate buffer (pH 4.0) then with sodium dihydrogen phosphate buffer (pH 6.0), dry the solution over anhydrous sodium sulfate and evaporate to a residue. Crystallize the residue from acetone to obtain antibiotic 68-1147 complex, yield = 6.6 g.

Prepare a chromatographic column with 300 g. of silica gel (Type 60, Stahl). Adsorb the antibiotic complex from a mixture of acetone:benzene (4:10) and develop the column with the same solvent mixture. Monitor the chromatographic separation by thin layer chromatography using silica gel and an acetone:benzene (1:2) solvent mixture. Combine fractions having Rf values of 0.2→0.4 and evaporate to dryness-yield 2.2 g.

Rechromatograph the solids on silica gel plates 250 μ thick using acetone:benzene (5.5:10) by spotting 10 mg/plate. Monitor the separation as described above to obtain thereby 1.0 g. of 68-1147 I,Rf (0.36) M.P. 229°–231° C dec., $[\alpha]_D^{26°} = -87.5°$ (0.4% dioxane) and (0.64 g) 68-1147 II, M.P. decomposes at about 300° C, $[\alpha]_D^{26°} = -65.5°$ (0.4% dioxane).

We claim:

1. A process for producing antibiotic 68-1147 complex which comprises cultivating an antibiotic 68-1147 producing strain of *Micromonospora arborensis* NRRL 8041 in an aqueous nutrient medium containing assimilable sources of carbon and nitrogen, under aerobic conditions until substantial antibiotic activity is imparted to said medium and isolating antibiotic 68-1147 complex therefrom.

2. A process according to claim 1 wherein the microorganism is cultivated at a temperature between 20° and 40° 1 C for from about 2 to about 7 days and from about pH 6.0 to about pH 8.5.

3. A process according to claim 2 wherein the microorganism is cultivated at a temperature between 28° and 35° C and from about pH 7.0 to about pH 8.0.

4. A process according to claim 3 including the step of separating antibiotic 68-1147 I and antibiotic 68-1147 II of the thus isolated antibiotic 68-1147 complex by chromatography on silica gel.

5. Antibiotic 68-1147 I, a compound which:
   a. is effective in inhibiting the growth of various bacteria, especially Gram positive bacteria;
   b. has an optical rotation $[\alpha]_D^{26°} = -87.5°$ (C, 0.4%, dioxane)
   c. has a characteristic ultraviolet absorption spectrum in trifluoroethanol as follows:

| $\lambda$ max | $E_{cm}^{1\%}$ |
|---|---|
| 202 m$\mu$ | 53.55 |
| 247 | 32.55 |
| 308 | 10.72 | d. has the following elemental analysis: C, 49.46; H, 5.20; N, 14.88; O, 16.18; S, 10.47;
   e. has a melting point of 229°– 231° C dec.
   f. has a characteristic infrared absorption spectrum in mineral oil (Nujol) with absorption at:

| | | |
|---|---|---|
| 3.05 m,sp | 7.30 m,sp | 9.75 w,sp |
| 3.45 s,sp | 7.45 sh | 9.95 sh |
| 5.78 w,sp | 7.65 w,sp | 10.58 w,br |
| 6.08 s | 8.30 w,sp | 10.70 w,br |
| 6.31 w,sp | 9.00 w,sp | 11.20 w,br |
| 6.60 s | 9.15 w,br | 11.30 sh |
| 6.65 s | 9.50 w,br | 11.90 microns w,br |
| 6.75 s | 9.40 w,br | | g. contains the following aminoacids: threonine, proline, alanine, cysteine, isoluecine and tyrosine.

6. Antibiotic 68-1147 II, made by the process of claim 4 being further characterized as having the following characteristics:
   a. is effective in inhibiting the growth of various bacteria, especially Gram positive bacteria;
   b. has an optical rotation $[\alpha]_D^{26°} = -65.5°$ (C, 0.4%, dioxane);
   c. has a characteristic ultraviolet absorption spectrum in trifluoroethanol as follows:

| $\lambda$ max | $\Sigma_{cm}^{1\%}$ |
|---|---|
| 240 m$\mu$ | 18.84 |
| 300 m$\mu$ | 5.42 | d. has the following elemental analysis: C,50.24; H, 4.98; N, 15.87; O, 16.24; S, 12.67 (by difference);
   e. has a melting point $\cong$300° C dec., and
   f. contains the following amino acids: threonine, proline, alanine, isoleucine and tyrosine.

* * * * *